(12) United States Patent
Smith et al.

(10) Patent No.: US 6,476,541 B1
(45) Date of Patent: Nov. 5, 2002

(54) OPTICALLY CONTROLLED ULTRASONIC SENSOR

(75) Inventors: Lowell Scott Smith, Niskayuna, NY (US); Anil Raj Duggal, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/790,779

(22) Filed: Feb. 23, 2001

(51) Int. Cl.$^7$ .............................................. H01L 41/08
(52) U.S. Cl. ....................... 310/334; 310/358
(58) Field of Search ................. 310/357, 358, 310/359, 800, 311

(56) References Cited

U.S. PATENT DOCUMENTS

| | | | | |
|---|---|---|---|---|
| 3,893,215 A | * | 7/1975 | Yasar | 310/358 Y |
| 3,922,622 A | * | 11/1975 | Boyd et al. | 333/30 R |
| 3,987,226 A | * | 10/1976 | Yasar | 428/44 |
| 4,077,558 A | * | 3/1978 | Carlson et al. | 228/121 |
| 4,683,396 A | * | 7/1987 | Takeuchi et al. | 310/358 |
| 5,311,321 A | * | 5/1994 | Crowley | 348/760 |
| 5,353,262 A | | 10/1994 | Yakymshyn et al. | 367/149 |
| 5,636,181 A | | 6/1997 | Duggal | 367/149 |

OTHER PUBLICATIONS

Smith, "The Role of Piezocomposites in Ultrasound Transducers," 1989 IEEE Ultrasonics Symposium, pp. 755–766 (1989).

Klicker et al., "Composites of PZT and Epoxy for Hydrostatic Transducer Applications," J. Amer. Ceram. Soc., vol. 64, No. 1, pp. 5–8 (1981).

Emery et al., "Ultrasonic Imaging Using Optoelectronic Transmitters," Ultrasonic Imaging, vol. 20, pp. 113–131 (1998).

* cited by examiner

Primary Examiner—Mark O. Budd
(74) Attorney, Agent, or Firm—Jill M. Breedlove; Christian G. Cabou

(57) ABSTRACT

An ultrasonic probe optically coupled to an electronic console comprises a multiplicity of transducer elements. Each transducer element is capable of transmitting and detecting ultrasound waves. Each transducer element constitutes a piezocomposite structure comprising mutually parallel rods of two types embedded in a passive polymer matrix: piezoelectric rods and micro-cavity laser rods. The piezoelectric rods are optically activated to generate an acoustic compression wave transmitted from the front face of the piezocomposite structure. The micro-cavity lasers produce a frequency-modulated optical signal having a frequency shift which is a function of a strain produced in the lasing medium by a returning acoustic wave impinging on the piezocomposite structure.

22 Claims, 3 Drawing Sheets

OPTICALLY CONTROLLED ULTRASONIC SENSOR

This invention relates to phased-array ultrasound imaging systems and, more particularly, to methods and apparatus for facilitating communication between an ultrasonic transducer probe and an electronic console that performs beamforming and signal processing.

BACKGROUND OF THE INVENTION

Ultrasonic or acoustic sensing techniques have earned a pre-eminent position in a variety of fields including medicine, nondestructive testing and process monitoring, geophysics, and sonar surveillance. For several decades, applications have exploited the relatively low expense, reliability, and enormous versatility of this modality. A strong theoretical understanding of ultrasonics has been developed in parallel with this practical knowledge, so that improved performance has steadily continued. Much of today's research and development is aimed at increasing the number of elements in an ultrasonic array, decreasing the size of the elements, or achieving both simultaneously. The resulting arrays would provide improved spatial or temporal resolution either by using higher frequencies, or by using true two-dimensional arrays for volumetric imaging. However, such advances present formidable technical challenges. Two major obstacles are element impedance and fabrication issues, and issues concerned with cabling between the sensor head and the electronic console.

Most ultrasonic transducers rely on the piezoelectric effect to detect and generate acoustic waves. The design and fabrication of piezoelectric elements remains as much an art as a science, and proves increasingly difficult as element size is decreased or element number increased. Difficulties are in part mechanical: the actual construction and handling of many extremely small components, the fabrication and "dicing" of multi-element arrays, reproducibility, and yield. Another major concern is electrical: as an element decreases in size, its impedance increases. Impedance matching, critical to signal sensitivity, presents additional complications. In particular, as the element impedance increases relative to the combined impedances of the coaxial line and the receiver circuit, less signal reaches the receiver circuit. Thus, for a given piezoelectric material, a reduction in element size is accompanied by a reduction in signal sensitivity.

The electrical cable bundle linking an ultrasonic array and its electronics also presents problems. Proper shielding is vital, since the cables are a major noise source. Cable length is restricted by the wire impedance relative to the element impedance. Furthermore, fabrication becomes more difficult as the number of array elements, and consequently the number of connecting wires, is increased. To avoid fabricating a hopelessly bulky and unmanageable cable, manufacturers must continually decrease the size of their coaxial wires. Although present technology can enable about 100 coaxial lines to fit into a narrow (a few millimeters in diameter) cable, cable size reductions cannot be continued indefinitely; at such small wire diameters, DC (direct current) resistance becomes significantly high. Additional practical difficulties are presented simply in using extremely small wires, for instance, in wire bonding or soldering.

In response to these challenges, optic, instead of electronic, control of piezoelectric elements has been proposed. Acquisition and control opto-electronics could be coupled to a transducer head via a fiber optic bundle; communication with the compact head would be by optical fibers. With present fiber optic technology, enough fibers for a 100×10 element array could fit inside a cable only a few millimeters in diameter. A thinner, more flexible cable of virtually any length offers added operator convenience, especially for medical use. Medical implementations such as ultrasonic catheters and endoscopes could similarly benefit. Radioactive or other harsh environments could be inspected remotely, without damage to sensitive electronics. Ultrasonic evaluation of large, complex, and limited-access components, such as long tubes, bores, or piping, could be performed more easily. In addition, optical methods of communicating between a piezoelectric transducer array and an electronic console could enable new applications that are not feasible with present technology, for instance in remote sensing or "smart structures".

To facilitate optical communication between a transducer probe and an electronic console, it has been proposed to detect ultrasound using a micro-cavity laser, which requires only an optical connection to the transducer probe. The proposed prior art method uses a monolithic laser cavity, such as a microchip laser, in place of a piezoelectric crystal. In its simplest form, the microchip consists of small "chip" (of area $\approx 1$ mm$^2$) of a lasing medium, which is cut and polished flat on two parallel sides. By depositing dielectric mirror coatings on these flat sides, a laser cavity is defined. Lasing is accomplished by optically pumping with a separate laser tuned to an absorption band of the microchip. The materials that have seen the most development as microchip laser media include neodymium-doped crystals such as $Nd_xY_{3-x}Al_5O_{12}$ (Nd:YAG) and $Nd_xY_{1-x}VO_4$ (Nd:YVO$_4$). These crystals have exhibited quite efficient CW lasing ($\approx 30\%$ optical efficiency) when pumped either by a Ti:sapphire laser or a diode laser.

The proposed prior art method relies on the fact that when the cavity length (L) of the laser is changed, the optical frequency ($v_o$) emitted by the laser changes such that the fractional length change is equal to the fractional frequency change as set forth in the following equation:

$$\frac{\Delta v}{v_o} = \frac{\Delta L}{L} \qquad (1)$$

When the laser cavity is placed in a time-varying acoustic field, the cavity length of the laser should be modulated with the same time dependence as the acoustic field and with an amplitude related to the amplitude of the acoustic field. As a result, Eq. (1) shows that the optical energy output of the laser should be frequency modulated with a time dependence and amplitude determined by the respective time dependence and amplitude of the acoustic field. The frequency-modulated optical energy can then be demodulated and converted into an electrical output signal remotely from the microchip for signal analysis. The original time-varying acoustic field can be recovered by frequency demodulating the optical signal using a slope filter.

In order for the aforesaid detection method to be advantageous, the laser detector must be of small size (e.g., active area <1 mm$^2$) and free from any electrical connections. Microchip laser technology satisfies these requirements. A microchip laser comprises a "chip" of a lasing medium such as neodymium-doped yttrium aluminum garnet (Nd:YAG), fabricated with dielectric mirror coatings on two ends so that it can be optically pumped. When pumped by a wavelength corresponding to an absorption band, the lasing process can be accomplished with a remotely situated, low-power laser delivered through an optical fiber. The mirror coatings can be arranged so that the microchip laser output energy returns through the same fiber. Since the return light is a different wavelength from the pump light, it can be separated with a wavelength demultiplexer and then frequency demodulated to extract the optical signal component determined by the time dependence and amplitude of the acoustic field.

Equation (1) shows that the frequency shift experienced by the microchip laser output energy depends on the macroscopic strain ($\Delta L/L$) experienced by the microchip. The macroscopic strain is related to the microscopic strain $S(x,t)$ by the following equation:

$$\frac{\Delta L(t)}{L} = \frac{1}{L}\int_o^L S(x, t)\,dx. \qquad (2)$$

where x represents position along the thickness of the micro-cavity laser and t is time. Given any arbitrary acoustic disturbance in the microchip, the change in lasing frequency can be calculated using Eqs. (1) and (2). The microscopic strain that develops in the microchip in response to an incident acoustic wave depends sensitively on the ratio of the microchip cavity length to the acoustic wavelength, the acoustic impedance of the microchip relative to the medium in which it is embedded, and the acoustic impedance of any other structures such as acoustic matching layers attached to the microchip.

Although micro-cavity lasers have been demonstrated to detect ultrasound at frequencies and intensities compatible with medical imaging, it is difficult to construct a suitable transmitter in the same structure as the laser detector. There is a need for a structure which overcomes this difficulty.

SUMMARY OF THE INVENTION

The invention overcomes the foregoing difficulty by incorporating micro-cavity lasers in a piezocomposite material of an ultrasonic transducer. As used herein, the term "piezocomposite" refers to a combination of a piezoelectric material (e.g., piezoelectric ceramic or single-crystal piezoelectric material) and a non-piezoelectric polymer to form a new piezoelectric material.

Piezocomposite materials were introduced in the past to reduce the lateral mechanical coupling inherent in bulk piezoelectric ceramic. In accordance with the conventional technique, isolated long, thin piezoceramic rods (e.g., PZT) are interspersed in and held parallel to each other by a passive polymer matrix. As long as the spacing is small compared to the wavelength, the transducer element will vibrate uniformly, as a whole, with the elastic properties of the effective medium formed by the piezoceramic and the polymer. The resulting elements are effective as both transmitters and receivers of ultrasound.

Also well known in the prior art are micro-cavity lasers used as detectors of ultrasound. The cavity responds to acoustic pressure changes by changing its length. As a laser cavity, the resonant frequency of the cavity, and hence the frequency of the output beam, is very sensitive to the length of the cavity. Since the optical beam can be examined with high-finesse optical components, it is possible to detect small frequency shifts with great accuracy without direct electrical connections. The output optical energy of the micro-cavity laser is simply coupled to a fiber optic cable and transmitted to the console, where the optical system frequency modulator detects the laser output optical energy.

The materials used for micro-cavity lasers are typically transition metal and rare-earth doped glasses. These materials tend to be rather dense and have specific acoustic impedances in the same range as commonly used piezoceramic materials like PZT. These acoustic impedances are often in the range of 25 to 40 MRayls (1 Rayleigh or Rayl is 1 kilogram/square meter/second). Since these elastic properties are comparable to the piezoelectric material properties, it is possible to replace some of the rods in a piezoelectric-polymer composite with micro-cavity laser rods (i.e., micro-cavity lasers in the shape of rods) without substantially changing the modes of vibration of the resulting structure. The resulting assembly is capable of transmitting and receiving ultrasound energy like a conventional composite transducer. By using the micro-cavity laser segments, received ultrasound can be sensed without requiring electrical connections to convey the acquired data from the array to the electronic console for beamforming and signal processing.

In another aspect, the invention is directed to the foregoing composite structure, comprising piezoelectric (e.g., ceramic or single crystal) rods and micro-cavity laser rods embedded in a passive polymer matrix, and a method for manufacturing such a composite structure.

In another aspect, the invention is directed to facilitating communication between a multi-element ultrasonic transducer probe and an electronic console, e.g., a console comprising an electronic beamformer. The probe and the console are coupled by optical means, e.g., optical fibers. Each transducer element in the probe comprises a polymer matrix having rods of piezoelectric material and micro-cavity laser rods embedded therein.

In accordance with a preferred embodiment of the invention, the probe receives high-voltage electrical energy from a power source via an electrical cable and receives a multiplicity of optical beamforming signals from a transmit beamformer via a respective multiplicity of optical fibers. The electrical power is distributed to the transducer elements via a multiplicity of optically controlled switches which receive the optical beamforming signals. As a result, the piezoelectric material of respective transducer elements is activated to transmit an ultrasonic beam.

In accordance with another preferred embodiment of the invention, the ultrasonic echoes are detected by micro-cavity lasers incorporated in the transducer elements. The resulting optical output signals of the micro-cavity lasers are frequency demodulated to isolate the component corresponding to the received acoustic signal. The frequency-demodulated optical signals are then sent to the electronic receive beamformer. Preferably, the frequency demodulators are located within the console and are coupled to the probe via optical fibers.

DETAILED DESCRIPTION OF THE PREFERRED EMBODIMENTS

Figure 1:
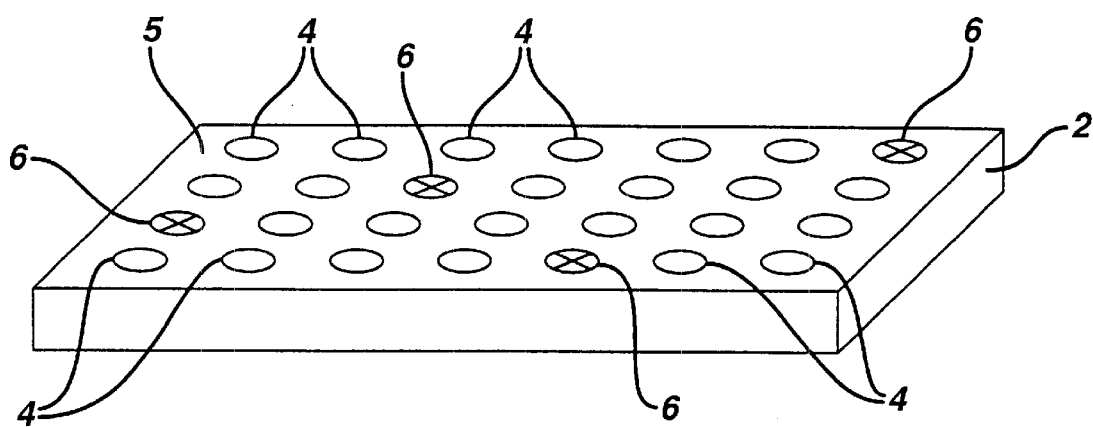
FIG. 1 is a schematic, oblique view of a transducer element comprising a polymer matrix having piezoelectric rods and micro-cavity laser rods embedded therein in accordance with a preferred embodiment of the invention.

An ultrasonic transducer element in accordance with a preferred embodiment of the invention is shown in FIG. 1.

It will be readily appreciated that a multiplicity of such elements can be arranged in a one- or two-dimensional array in a probe which is optically coupled to an electronic console. Each transducer element comprises a polymer matrix 2 in the shape of a block having three sets of mutually parallel faces. A multiplicity of mutually parallel rods, of two types 4 and 6, are embedded in the polymer matrix, preferably spaced at regular intervals. The rods are generally perpendicular to the opposing faces having the largest area and which form the front and rear faces of the transducer element. The element interfaces with the acoustic medium via the front face 5. Each rod 4 is comprised of piezoelectric (e.g., ceramic or single crystal) material, while each rod 6 comprises a micro-cavity laser rod having an optical cavity extending along the length of the rod and having opposing faces at the opposing ends of the rod. Each transducer element includes at least one micro-cavity laser. The ends of the micro-cavity laser optical cavity are coated on opposing sides with dielectric mirrors or reflectors, as described in more detail hereinafter with reference to FIG. 3. The micro-cavity laser is designed so that all optical access to and from the laser occurs on one side, and all acoustic access for the purpose of ultrasonic detection occurs on the other side. The coated laser ends must be precisely parallel to each other to ensure efficient lasing.

The piezoelectric rods facilitate transmission of ultrasound from the transducer element, while the micro-cavity lasers permit reception with flexible fiber optic connections. The micro-cavity laser materials preferably have specific acoustic impedances in the same range as the piezoelectric rod materials. The laser material should also have elastic properties comparable to those of the piezoelectric material; however, the detailed design of the composite is intended to make the optical fibers (i.e., rods) move together with the polymer matrix, so that considerable latitude in the material properties is possible. In particular, it is possible to incorporate micro-cavity laser materials with quite different acoustic impedances.

In conventional manner, electrodes 34 and 36 (shown in FIG. 2) are applied to the opposing front and rear faces of the transducer element depicted in FIG. 1. The resulting assembly can transmit and receive ultrasound like a conventional piezocomposite transducer, although the electrode structure may be slightly more complex than some traditional piezocomposite devices. For transmission, a uniform electric field is typically applied over the entire device; however, the effect of the field is greatly confined to the piezoelectric segments, which have an enormous dielectric constant (>2000) compared to the polymer or laser material (<20). Therefore, even if no electrode were present over the laser material, the rest of the device would experience a strain when a voltage is applied. The presence of an electrode over the micro-cavity laser would compromise its optical efficiency. Nonetheless, it may be possible to achieve acceptable results with so-called transparent electrodes, which are fabricated of materials such as tin oxide.

One way to fabricate this structure is to start with fibers of both piezoelectric and micro-cavity laser material. Piezoelectric fibers have been reported having diameters down to a few hundreds of microns with tolerances of 1–2%. Given a collection of fibers, they can be arranged in a set of parallel alignment fixtures. For example, a fixture comprised of two brass disks in which holes have been drilled can be used to align the fibers, i.e., rods. The drilled disks are aligned and filled with rods, and the filled rack is placed in a tube having two closed ends and a slot in one side. The polymer is poured into the plastic tube via the slot, flowing around the rods. If necessary, the tube can be placed under vacuum to prevent formation of air bubbles during the filling operation. After the tube has been filled, the polymer is cured. Finally, plates perpendicular to the fiber axes are sliced off and coated with electrodes. A slightly different approach would coat the initial fibers with a polymer or thermoplastic cladding, as is well known in the art. The coated fibers would then be laid up in a fixed geometry (e.g., hexagonal close packing) before subsequent processing to fuse the plastic together. For thermoplastics, this can be accomplished by extrusion through a hot die. The positions of both piezoelectric and micro-cavity laser fibers in the assembly must be controlled and maintained. While FIG. 1 shows a pattern in which every eighth rod 6 (indicated by X's) is a micro-cavity laser with the other rods 4 being piezoelectric material, it will readily be appreciated that other patterns and ratios can be used.

An ultrasound imaging system incorporating transducer elements of the type described above is depicted in FIG. 2. The composite material depicted in FIG. 1, however, is not limited in its application to transducer elements for use in an ultrasound imaging system. The same material can be used in probes for non-destructive testing, sonar surveillance, geophysics, etc.

In order to replace the conventional coaxial cable bundle with a much smaller optical fiber cable bundle, methods for both transmission and reception are needed. As discussed below, the micro-cavity laser is used to detect ultrasound over a fiber optic cable; however, transmission requires a different strategy. An optical signal, by itself, is not sufficient to produce the necessary power to generate ultrasound for most medical applications; instead, the optical signal must be used to control an electronic signal with sufficient power to do the electromechanical work necessary to drive the various transducer elements.

Figure 2:
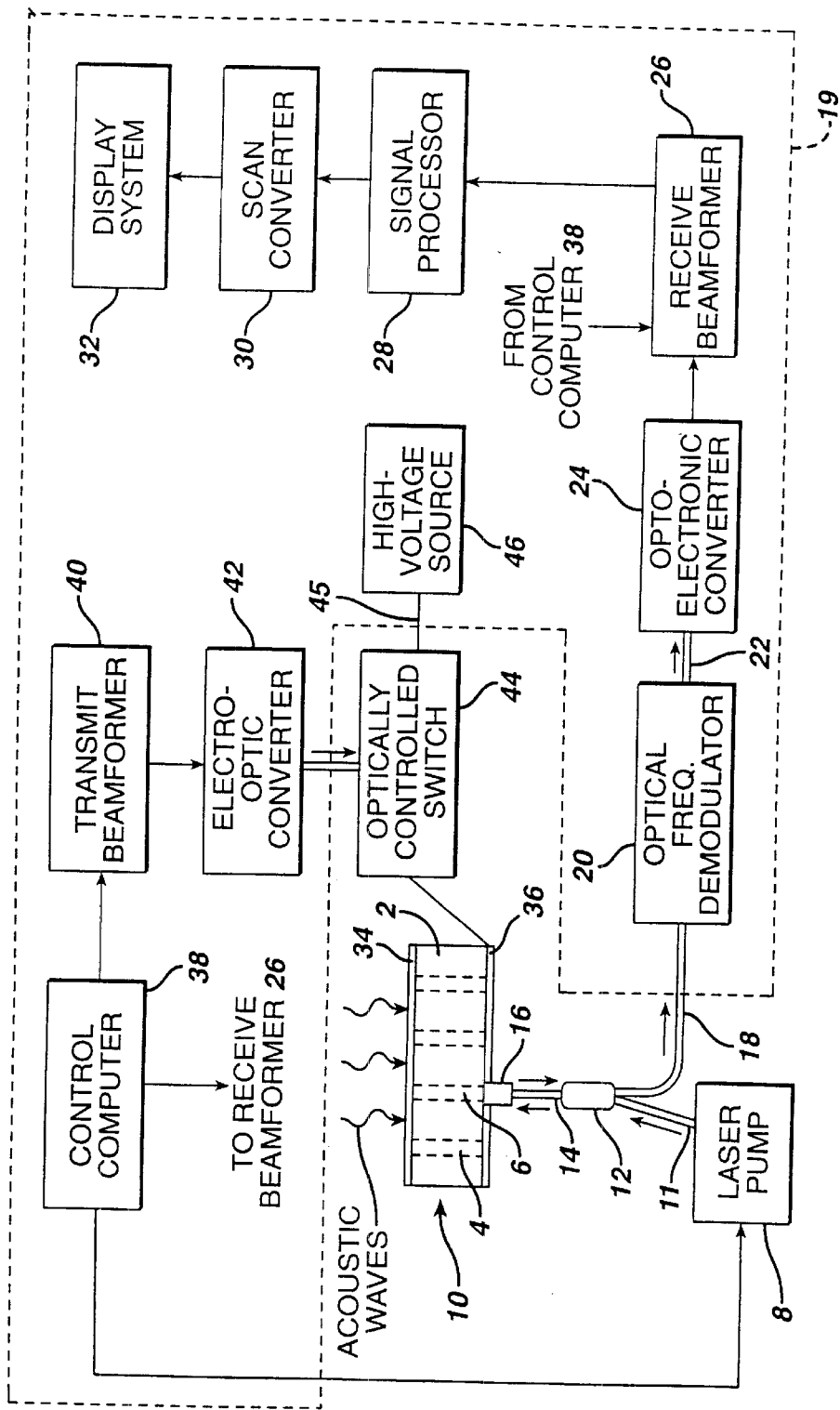
FIG. 2 is a block diagram of an ultrasound imaging system employing the transducer element shown in FIG. 1.

FIG. 2 shows a high-voltage source 46 energizing a probe via an electrical bus 45. At the probe, the high-voltage electrical energy is distributed to the individual transmitter elements 10 through optically controlled switches 44. These switches may be photo-transistors, optically activated thyristors, or silicon-controlled rectifiers (SCRs). An optical signal, typically generated in a console 19 and conducted to the probe on an optical fiber 43, activates a switch 44, thus applying the high voltage to the desired element at the appropriate time for transmit beamforming. In particular, a control computer 38 provides transmit beamforming time delays to a transmit beamformer 40, which in turn generates electrical pulses that are converted into optical pulses by an electro-optical converter 42. These optical pulses control the state of optically controlled switches 44, which pass the high-voltage electrical energy when switched to an ON state by an optical pulse. The voltage is applied across a ground electrode 34 and signal electrode 36 of transducer element 10 to generate an acoustic compression wave which propagates into the acoustic medium to which the front face of the transducer elements is coupled. In a conventional manner, the transmit beamforming time delays can be varied from firing to firing to scan the transmit focal zone over a region of interest.

During reception, the signal processing coefficients change continuously so that the received signals are always being focused whereas, during transmission, a reasonable choice for the coefficients is picked and an ultrasound beam is fired off, so that one set of coefficients suffices for that portion of the image. Therefore, it may be possible to segment the aperture of the probe in relatively larger segments for transmission than is possible for reception.

Alternatively, fewer elements may be needed for transmission than reception. Therefore, the required electronics in the probe head may be minimized if the electronics are required only for transmission and not reception.

Following each transmit firing, each transducer element detects the returning acoustic compression waves. More precisely, the micro-cavity lasers 6 (only one of which is shown in FIG. 2) in each transducer element detect the returning acoustic compression waves. This is accomplished as follows. A laser pump 8 is coupled to an optical cavity (not shown in FIG. 2) of micro-cavity laser 6 via an optical fiber 11, a wavelength-selective coupler 12, an optical fiber 14 and an optical coupler 16. Preferably, there is one laser pump for each respective transducer element, and the laser pump communicates with all of the micro-cavity lasers of a given transducer element.

Wavelength selective coupler 12 passes optical signals of different wavelengths along different paths. Thus, light generated by laser pump 8 to excite micro-cavity laser 6 is of a frequency such that it is directed along optical fiber 14 to optical coupler 16. The modulated light signal generated by micro-cavity laser 6 when it is lasing, and which is of a different optical frequency than the excitation signal from laser pump 8, is passed on an optical fiber 18 from the probe to an optical frequency demodulator 20, typically located on electronic console 19. Optical coupler 16 advantageously comprises lenses disposed to efficiently couple light into micro-cavity laser 6 from laser pump 8 and couple light generated in laser 6 into optical fiber 14 for transmission to frequency demodulator 20. Optical fiber 14 is one of many optical fibers forming an optical fiber bundle connecting the probe to the console (not shown). Within a single signal processing transducer element there may be one or more microcavity laser structures. The simplest arrangement is to have one optical communication fiber per microcavity laser, but it is also desirable to have only one communication fiber per transducer element. Hence the optical coupler may act as a multiplexer, reducing the number of communication fibers required. The same optical coupler may thus be used to couple more than one microcavity laser in the element to its associated fiber.

Optical frequency demodulator 20 is designed to recover the optical signal component corresponding to the acoustic signal. For example, the frequency demodulation may be performed by a Fabry-Perot etalon acting as a slope filter. The frequency-demodulated signal is transmitted to an opto-electronic converter 24 in electronic console 19 via an optical fiber 22. Preferably there is one frequency demodulator per transducer element.

The optical signals are converted to electrical signals by opto-electronic converters 24, e.g., photodiodes, and the resulting receive signals are sent to a conventional receive beamformer 26 operated under control of control computer 38. Receive beamformer 26 combines the separate echo signals from each transducer element to produce a single beamsummed signal that is used to produce a line in an image. The receive beamformer output signal is sent to a signal processor 28. In the conventional B-mode imaging mode, vectors of filtered I (in-phase) and Q (quadrature phase) acoustic data are sent to signal processor 28, which converts the I and Q acoustic data into a log-compressed version of the signal envelope. The time-varying amplitude of the signal envelope is imaged as a gray scale. The envelope of a baseband signal is the magnitude of the vector which I and Q represent. The magnitude (i.e., intensity) of the signal is the square root of the sum of the squares of the orthogonal components, i.e., $(I^2+Q^2)^{1/2}$. The B-mode intensity data are supplied to a scan converter 30, which accepts the processed vectors of B-mode intensity data and interpolates where necessary, and transforms the B-mode intensity data from polar coordinate (R–θ) sector format or Cartesian coordinate linear format to appropriately scaled Cartesian coordinate display pixel intensity data. The scan-converted frames are then passed to a video processor (within display system 32), which converts the pixel intensity data to the video frame rate and then maps the pixel intensity data to a gray-scale mapping for video display. The gray-scale image frames are then displayed by a display monitor of display system 32. The displayed image represents the tissue and/or blood flow in a plane through the body being imaged.

System control is centered in control computer 38, which accepts operator inputs through an operator interface (not shown) and in turn controls the various subsystems and thus performs system level control functions. A system control bus (not shown) provides an interface from the host computer to the subsystems.

In the receive mode, laser pump 8 generates temporally varying excitation energy which is applied to micro-cavity laser 6 and is sufficient to cause lasing at a particular frequency. Acoustic energy produced by the transducer and reflected from the sample under examination is incident on the transducer and modulates the optical frequency of micro-cavity laser 6. Laser pump 8 is controlled, e.g., by control computer 38 to provide the desired level of excitation energy to micro-cavity laser 6 at the appropriate time. As acoustic energy reflected from the sample is incident on transducer 10, the lasing medium is displaced along the optical path axis in response to compression and rarefaction from the incident acoustic energy. This displacement is manifested in variations in length L of optical cavity 50 (shown in FIG. 3) which, in turn, causes the frequency of the light generated by laser 8 to change in correspondence with the incident acoustic energy. As the amplitude of acoustic energy incident on transducer 10 increases, the variation in length of the optical cavity also increases and thus the variation in optical frequency similarly increases. Micro-cavity laser 6 is adapted to operate at a nominal optical frequency (no displacement of the optical cavity) that results in substantially linear variation of the optical frequency in response to the variations in length of the optical cavity.

Figure 3:
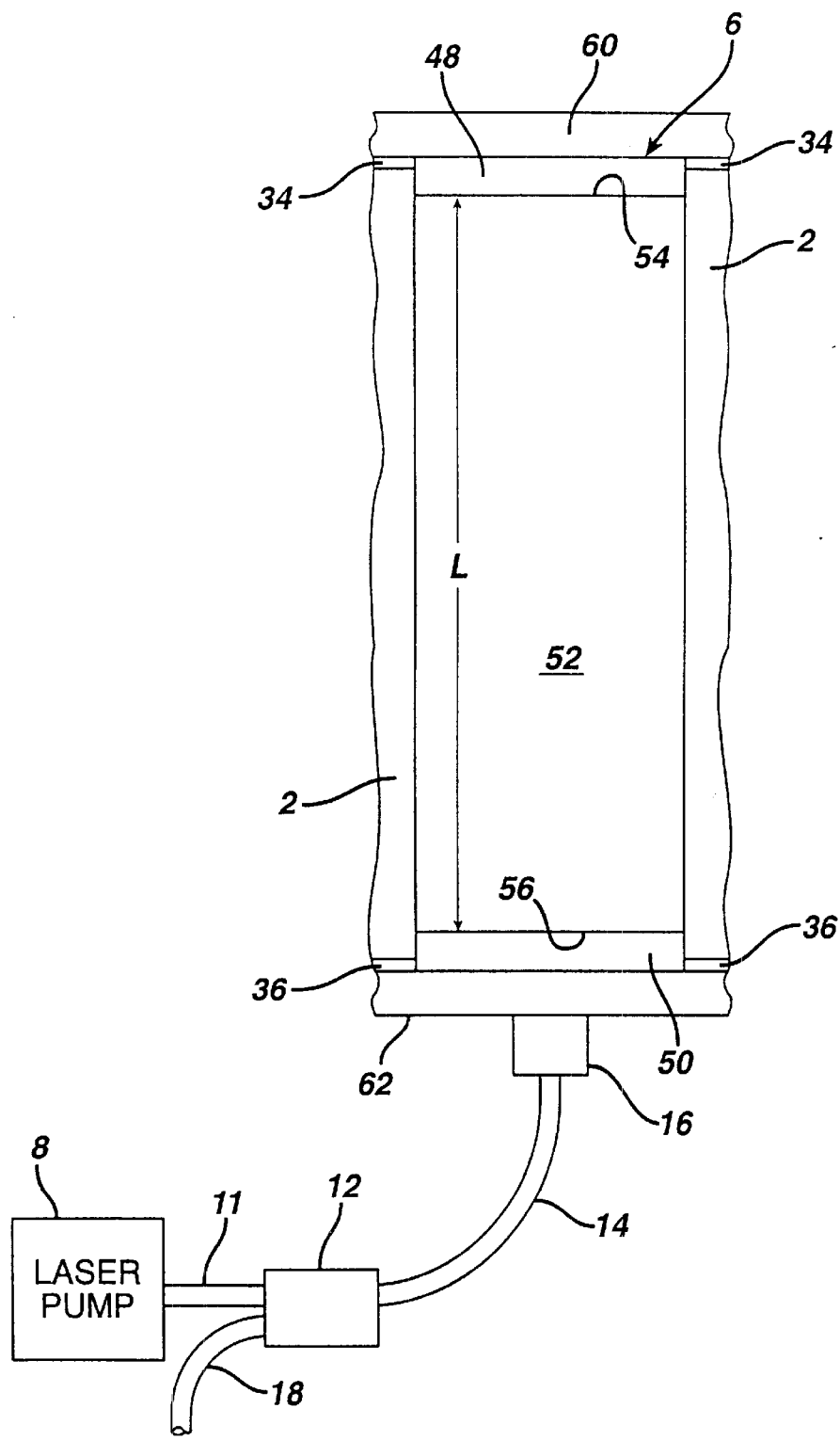
FIG. 3 is a schematic diagram of one type of acousto-optical transducer which can be used with the apparatus shown in FIGS. 1 and 2.

FIG. 3 illustrates in greater detail the structure of micro-cavity laser 6. The micro-cavity laser undergoes compression and rarefaction, in unison with the surrounding polymer matrix and adjacent piezoelectric rods, in response to acoustic energy impinging on the transducer element. The micro-cavity laser comprises an optical cavity disposed between a first reflector 48 and a second reflector 50, and in which a lasing medium 52 (also known as the gain crystal) is disposed. Lasing medium 52 comprises a material which provides the signal laser performance characteristics as described herein, such as variation of optical frequency generated in response to changes in length of the optical cavity. Examples of lasing media advantageously used in the invention include neodymium-doped yttrium aluminum garnet (Nd:YAG), neodymium-doped yttrium vanadate (Nd:YVO4), neodymium-doped glass (Nd:glass), chromium-doped lithium strontium aluminum fluoride (Cr:LiSAF), lithium strontium calcium aluminum fluoride (LiSCAF), and lithium calcium aluminum fluoride (LiCAF), or the like. Alternatively, an organic dye liquid lasing medium comprising rhodamine 6G or the like may be used as the lasing medium.

Lasing medium 52 has substantially plane-parallel end surfaces 54, 56 disposed opposite one another. First reflector 48 is disposed proximate to surface 54 and second reflector 50 is disposed proximate to surface 54 and second reflector 50 is disposed proximate to surface 56. The first and second reflectors are typically comprised of a dielectric material such as silicon nitride, silicon oxide, aluminum oxide, or the like, and are disposed immediately adjacent to the lasing medium surface, such as by deposition onto the respective surfaces 54, 56 of lasing medium 52. Reflectors 48, 50 are relatively thin, typically of 1 to 5 microns in thickness, or less. Dependent on the arrangement of micro-cavity laser 6, one reflector is typically substantially fully reflective, and the other partially transmissive, such that light generated when the gain crystal begins to lase can escape the optical cavity. In the micro-cavity laser illustrated in FIG. 3, first reflector 50 is slightly transmissive at the lasing wavelength, e.g., having a reflectance R of about 99% at the lasing wavelength. At the laser pump wavelength, however, first reflector 50 has a substantial transmittance, e.g., 80% or greater. Second reflector 48 is substantially totally reflective at both the lasing wavelength and the laser pump wavelength, having an R value of about 100%, e.g., 99.98%.

An optical path axis extends between, and substantially perpendicular to, opposing surfaces 54, 56 of lasing medium 52. The optical path axis is substantially parallel to the path of light energy reflected between first and second reflectors 48, 50, respectively, as the gain crystal lases. The cavity length L corresponds to the distance between the opposing reflective surfaces of the first and second reflectors. The length of the cavity supports longitudinal modes spaced sufficiently apart in wavelength such that only one mode overlaps the gain bandwidth of the crystal, and thus only one mode lases. The optical frequency at which micro-cavity laser 6 lases is a function of length L of the optical cavity. The thickness of lasing medium 52 is typically between about 10 and 1000 microns. Lasing medium 52 is selected such that the refractive index of the lasing material exhibits negligible changes in response to changes in length of the cavity. The absolute value of the change of optical frequency of micro-cavity laser 6 is directly proportional to, and primarily results from, the change in optical cavity length of micro-cavity laser 6. The optical frequency generated by micro-cavity laser 6 is thus modulable by acoustic energy incident on the transducer, since the micro-cavity laser is disposed such that the incident acoustic energy causes variations in the optical cavity length.

The ultrasonic sensor, in accordance with a preferred embodiment, additionally comprises one or more acoustic impedance matching layers 60 disposed over first reflector 48 and either an optically transparent acoustic backing layer 62 disposed over second reflector 50 or an acoustic backing with an optically transparent region. Acoustic impedance matching layer 60 is selected to provide a desired acoustic coupling between the transducer element and a couplant (not shown). For example, for a selected acoustic wavelength, optimal coupling is obtained when impedance matching layer 60 has a thickness of about one-quarter the acoustic wavelength in the matching layer material, and the acoustic impedance has a value which is the square of the product of the respective acoustic impedances of the two materials on either side of the impedance matching layer. Impedance matching layer 60 typically comprises a material which has the above-mentioned characteristics and is relatively non-attenuating, such as a polymer or the like. Acoustic backing layer 62 is disposed such that the incident acoustic energy that has passed through the transducer element is attenuated in the backing layer. Acoustic backing layer 62 typically comprises an organic material, such as an epoxy, with an appropriate filler mixed therein to provide the desired acoustic performance. The acoustic backing layer is substantially transparent (not highly absorbing or highly scattering) to laser wavelengths, at least over the region where light is entering or exiting the transducer. One way to increase the acoustic impedance of acoustic backing layer 62 is to mix heavy nanoparticles (which do not scatter or absorb light), such as heavy metals like tungsten or lead or their oxides, into the material of the backing layer. Since the wavelength of the light is much shorter than that of the sound, light is more sensitive than sound to scatterers.

Alternatively, another way of using microchip lasers to detect ultrasound that employs beating between two different polarizations of light coming out of the microchip is taught in U.S. Pat. No. 5,636,181, and can be used with the transducer elements disclosed and claimed herein. This technique has the advantage that the carrier frequency can be tuned so that it is within the bandwidth of electrical FM (frequency modulation) demodulation systems, thereby eliminating the need for an optical FM demodulation technique.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A transducer comprising a polymer matrix, a rod of piezoelectric material embedded in said polymer matrix, and an acousto-optical converter embedded in said polymer matrix.

2. The transducer as recited in claim 1, wherein said acousto-optical converter comprises a micro-cavity laser rod.

3. The transducer as recited in claim 1, wherein said polymer matrix comprises a front face, an end of said rod of piezoelectric material is generally flush with said front face, and said micro-cavity laser is generally parallel to said rod of piezoelectric material.

4. The transducer as recited in claim 2, wherein said micro-cavity laser rod is generally parallel to said rod of piezoelectric material.

5. The transducer as recited in claim 3, further comprising a metal electrode applied to said front face of said polymer matrix and in contact with said end of said rod of piezoelectric material.

6. The transducer as recited in claim 1, wherein said acousto-optical converter comprises a lasing medium having mutually parallel front and rear faces, a front reflective coating on said front face of said lasing medium and a rear reflective coating on said rear face of said lasing medium.

7. The transducer as recited in claim 6, further comprising a laser pump optically coupled to said lasing medium.

8. An ultrasonic probe comprising a multiplicity of transducers and a multiplicity of optical fibers respectively optically coupled to said transducers, wherein each of said transducers comprises a polymer matrix, a rod of piezoelectric material embedded in said polymer matrix, and an acousto-optical converter embedded in said polymer matrix.

9. The probe as recited in claim 8, wherein said acousto-optical converter comprises a micro-cavity laser rod.

10. The probe as recited in claim 9, wherein said polymer matrix comprises a front face, an end of said rod of piezoelectric material is generally flush with said front face, and said micro-cavity laser rod is generally parallel to said rod of piezoelectric material.

11. The probe as recited in claim 8, wherein each said acousto-optical converter comprises a lasing medium having mutually parallel front and rear faces, a front reflective coating on said front face of said lasing medium and a rear reflective coating on said rear face of said lasing medium, and wherein each of said transducers further comprises a laser pump optically coupled to said lasing medium.

12. The probe as recited in claim 8, further comprising an electrical distribution network for receiving electrical energy from a voltage source, said electrical distribution network being coupled to said transducers, and an additional multiplicity of optical fibers, wherein said voltage distribution network comprises a multiplicity of optically controlled switches for switchably coupling said transducers to said voltage source, each of said optically controlled switches being coupled to a respective optical fiber of said additional multiplicity of optical fibers.

13. The probe as recited in claim 11, further comprising means for frequency demodulating optical signals, said frequency demodulating means being optically coupled to the acousto-optical converters of said transducers.

14. A system comprising an ultrasonic probe, a console, and means for optically coupling said probe to said console, wherein said probe comprises a multiplicity of transducers optically coupled to the optical coupling means, each of said transducers comprising a polymer matrix, a rod of piezoelectric material embedded in said polymer matrix, and an acousto-optical converter embedded in said polymer matrix.

15. The system as recited in claim 14, wherein said console comprises an electronic receive beamformer and opto-electrical conversion means coupled to said optical coupling means and to said electronic receive beamformer.

16. The system as recited in claim 15, wherein said console further comprises signal processing means coupled to said beamformer, and a display system for displaying an image as a function of an image signal derived from an output of said signal processing means.

17. The system as recited in claim 14, wherein said acousto-optical converter comprises a micro-cavity laser rod.

18. The system as recited in claim 14, further comprising means for supplying electrical energy to said probe, wherein said probe comprises an electrical distribution network coupled to said transducers, said electrical distribution network comprising a multiplicity of optically controlled switches for switchably supplying electrical energy to said transducers, each of said optically controlled switches being coupled to a respective one of said transducers.

19. The system as recited in claim 18, wherein said console comprises an electronic transmit beamformer and electro-optical conversion means for coupling said transmit beamformer to said optically controlled switches.

20. An ultrasound imaging system comprising an ultrasonic probe, a console, and a multiplicity of optical fibers for optically coupling said probe to said console, wherein said probe comprises a multiplicity of transducers optically coupled to said multiplicity of optical fibers, each of said transducers comprising a polymer matrix, a rod of piezoelectric material embedded in said polymer matrix, and an acousto-optical converter embedded in said polymer matrix, each of the acousto-optical converters being respectively optically coupled to a respective optical fiber of said multiplicity of optical fibers.

21. The system as recited in claim 20, wherein each of said acousto-optical converters comprises a micro-cavity laser rod.

22. The system as recited in claim 20, further comprising means for supplying electrical energy to said probe and an additional multiplicity of optical fibers for optically coupling said probe to said console, wherein said probe comprises an electrical distribution network coupled to said transducers, said electrical distribution network comprising a multiplicity of optically controlled switches for switchably supplying electrical energy to said transducers, each of said optically controlled switches being coupled to a respective optical fiber of said additional multiplicity of optical fibers.

* * * * *